(12) United States Patent
Massetti et al.

(10) Patent No.: US 9,526,417 B1
(45) Date of Patent: Dec. 27, 2016

(54) PROJECTOR FOR ADAPTOR-LESS SMARTPHONE EYE IMAGING AND ASSOCIATED METHODS

(71) Applicant: OmniVision Technologies, Inc., Santa Clara, CA (US)

(72) Inventors: Dominic Massetti, Seal Beach, CA (US); Suganda Jutamulia, Berkeley, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/961,198

(22) Filed: Dec. 7, 2015

(51) Int. Cl.
*A61B 3/10* (2006.01)
*A61B 3/15* (2006.01)
*G02B 7/14* (2006.01)
*A61B 3/00* (2006.01)

(52) U.S. Cl.
CPC ............ *A61B 3/152* (2013.01); *A61B 3/0008* (2013.01); *A61B 3/0025* (2013.01); *G02B 7/14* (2013.01)

(58) Field of Classification Search
CPC ......... A61B 3/0008; A61B 3/14; A61B 3/145; A61B 3/156
USPC ....................................................... 351/221
See application file for complete search history.

(56) References Cited

U.S. PATENT DOCUMENTS

| 5,621,203 A * | 4/1997 | Swartz ............... G06K 7/10584 235/462.11 |
| 6,069,748 A | 5/2000 | Bietry |
| 2012/0320340 A1 | 12/2012 | Coleman, III et al. |
| 2014/0085603 A1 | 3/2014 | Su et al. |
| 2014/0268053 A1 | 9/2014 | Fabian et al. |
| 2015/0021228 A1 | 1/2015 | Su et al. |
| 2015/0103317 A1 | 4/2015 | Goldfain et al. |
| 2015/0245767 A1 * | 9/2015 | Northcott ............. A61B 3/1216 351/206 |
| 2015/0310670 A1 * | 10/2015 | Grossinger .......... G02B 27/017 345/156 |

OTHER PUBLICATIONS

V. Lakshminarayanan et at ""Smartphone Science" in Eye Care and Medicine," Optics and Photonics News, Jan. 2015, pp. 46-51.

* cited by examiner

*Primary Examiner* — Huy K Mai
(74) *Attorney, Agent, or Firm* — Lathrop & Gage LLP

(57) ABSTRACT

A projector and associated method allows adaptor-less smartphone eye imaging. The projector includes at least two line generators for projecting a pattern onto a face of a subject, and a structure for positioning the line generators relative to a camera of the smartphone. The pattern facilitates positioning of the smartphone relative to the subject's eye such that an image of the eye captured by the camera is optimal for evaluation.

15 Claims, 6 Drawing Sheets

PROJECTOR FOR ADAPTOR-LESS SMARTPHONE EYE IMAGING AND ASSOCIATED METHODS

BACKGROUND

Eye imaging is key to monitoring not only eye-related problems like glaucoma, cataracts, macular degeneration and refractive errors, but also many other chronic and systemic diseases such as diabetes, hypertension and neurological degeneration, all of which also impact vision. In 2010, the World Health Organization estimated that two-hundred and eighty-five million people worldwide exhibit some form of visual impairment. Thirty-nine million people are blind, but for eighty percent of these their sight could have been saved and/or their illness cured. However, ninety percent of these blinded people live in low-income countries. Smart-phone technology is expected to ease this problem if not totally solve it.

Smart-phones are conveniently portable and mobile. Furthermore, today's smart-phones are comparable in processing power to the high-performance personal computer systems of only a half-dozen years ago and to the supercomputers of several decades ago. At the end of 2014, there were some 1.75 billion smart-phone users worldwide, which creates the potential for profound worldwide penetration at the point of care. Smart-phones provide connectivity with the rest of the world in many ways, such as through mobile/cellular data connections, and through Wi-Fi networks. The smart-phone is also versatile, being programmable through "apps."

A wide variety of smart-phone apps enable the smart-phone to image an eye. However, these apps require an adaptor to position and align the eye relative to the smart-phone camera. FIG. 1 shows use of a prior-art adaptor 102 that positions a smartphone 104 to image an eye 106 of a subject 107. Eye 106 is positioned close to, or touching, adaptor 102, which may for example have a rubber eye-piece 103 proximate the eye. A section 108 of adaptor 102 is shaped, or otherwise configured, to constrain smartphone 104 such that a camera 105 of smartphone 104 is aligned with eye-piece 103 to facilitate alignment with eye 106. Adaptor 102 includes lenses, beam-splitters, and illuminators to facilitate capture of the image. To capture an image of the eye, adaptor 102 couples with smartphone 104, which runs an app 110 that is controlled by a user to capture an image of eye 106 when eye-piece 103 is positioned close to, or touching, eye 106. It is not possible to successfully capture an image of the eye using smartphone 104 and app 110 without using adaptor 102.

SUMMARY OF THE INVENTION

An advanced system positions and aligns a subject's eye relative to a smart-phone running an app without requiring or using an adaptor. Accordingly, the disclosed solution is less expensive than the prior-art adaptor, and since no adaptor is required, the widespread availability of the smart-phone as a mechanism of capturing images of the eye makes the solution widely available. Since there are no additional elements positioned between the eye and the smartphone, the quality of the image captured is not degraded. For example, a beam-splitter between the eye and the smart-phone reduces the light intensity captured by the smart-phone.

In one embodiment, a projector allows adaptor-less smart-phone eye imaging. The projector includes at least two line generators for projecting a pattern onto a face of a subject, and a structure for positioning the line generators relative to a camera of the smartphone. The pattern is configured to facilitate positioning of the smartphone relative to the subject's eye such that an image of the eye captured by the camera is optimal for evaluation.

In another embodiment, a method facilitates adaptor-less smartphone eye imaging. A projector is coupled proximate a camera of a smartphone and includes at least two line generators. Each of the at least two line generators generates a pattern of light that is projected into a field of view of the camera, such that the pattern of light is easily seen on the face of a subject when the camera is positioned optimally for capturing an image of the subject's eye.

DETAILED DESCRIPTION OF THE EMBODIMENTS

Figure 1:
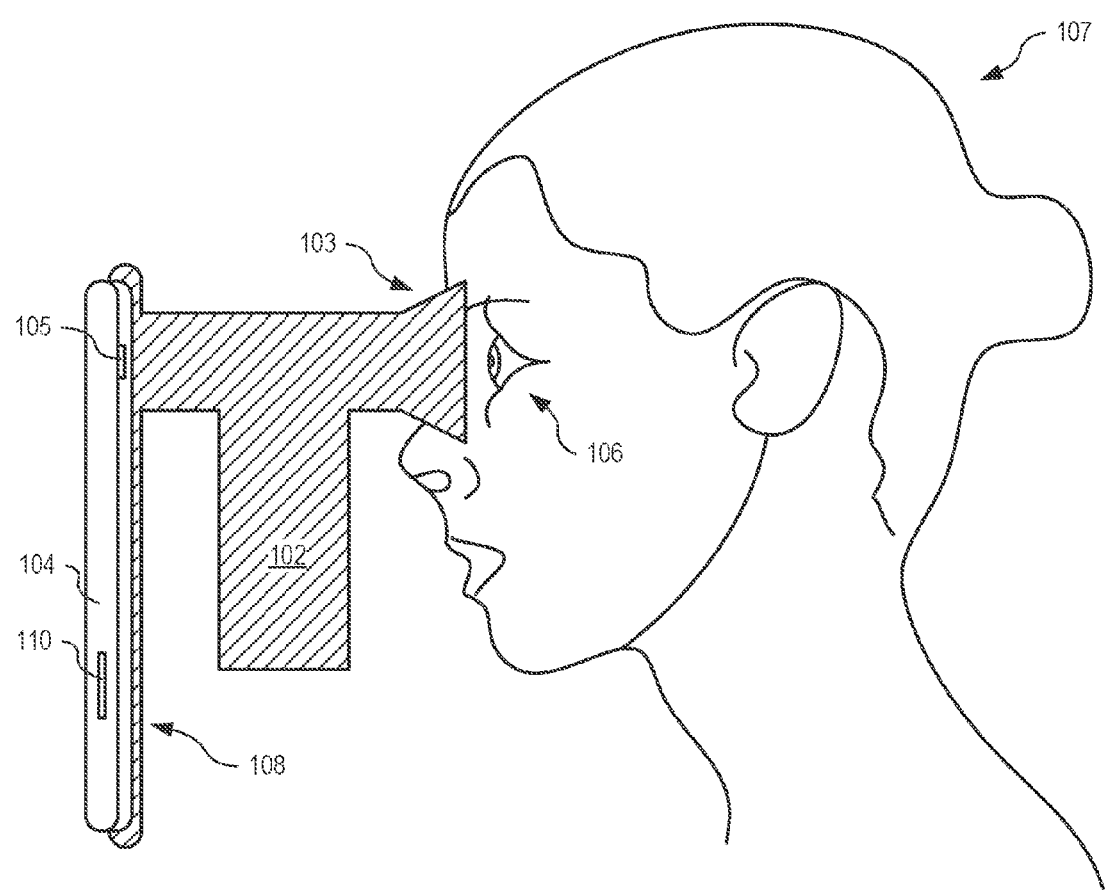
FIG. 1 shows a prior-art adaptor for imaging an eye using a smartphone.
Figure 2:
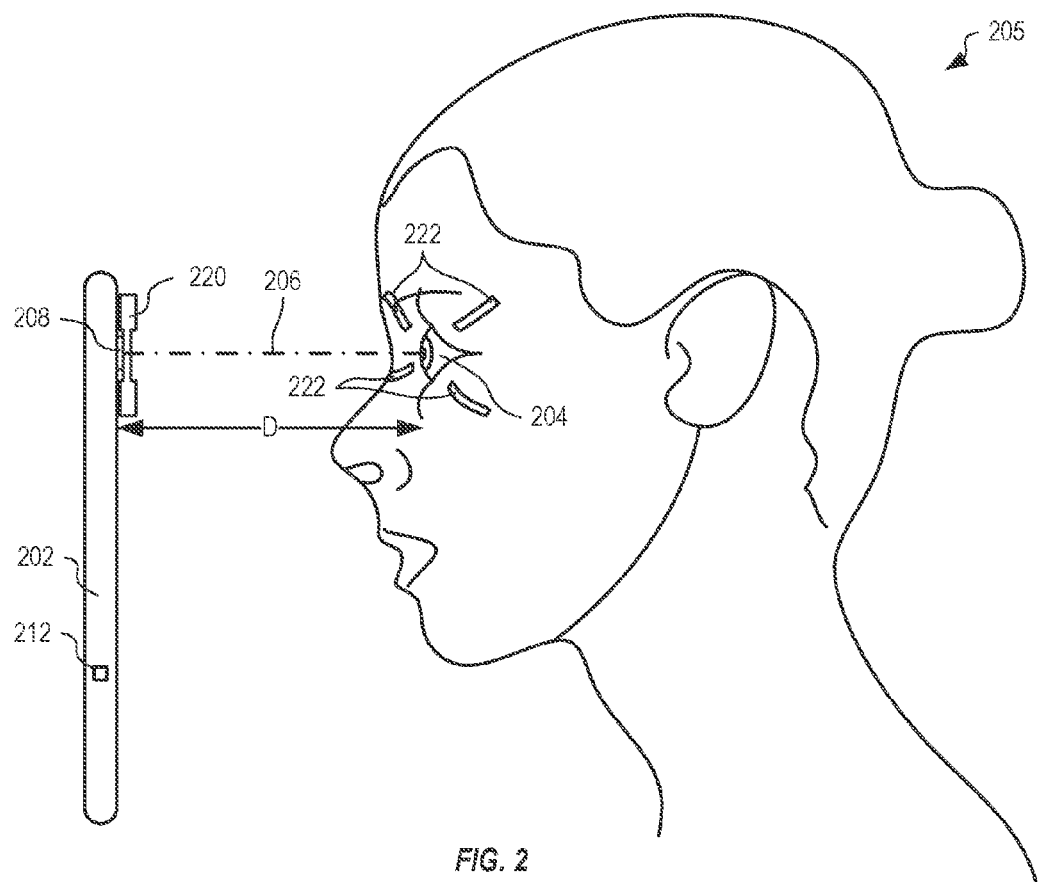
FIG. 2 shows a projector for adaptor-less smartphone eye imaging, in an embodiment.

FIG. 2 shows a projector 220 for adaptor-less smartphone eye imaging. In the example of FIG. 2, a smart-phone 202 is configured with projector 220 and positioned to capture, using a camera 208 of smartphone 202, an image 212 of an eye 204 of a subject 205. Smart-phone 202 may include a flash-light 210 (see FIG. 7) located close to camera 208 that may be used to illuminate eye 204 during capture of image 212. Image 212 is stored within a memory of smartphone 202 for example. Projector 220 projects a light pattern 222 into the field of view of camera 208, where the light pattern 222 is optically aligned with an optical axis 206 of camera 208. The user manipulates smartphone 202 to position light pattern 222 onto a face of subject 205, wherein light pattern 222 facilitates centering of eye 204 on optical axis 206 and at a distance D from eye 204 such that captured image 212 is optimal for further evaluation (e.g., for medical evaluation to identify disease). Light pattern 222 has one or both of mirror symmetry and rotational symmetry and is easily used by a user of smartphone 202 to align camera 208 with eye 204 of subject 205. In one embodiment, light pattern 222 is momentarily turned off when image 212 is captured, such that light pattern 222 does not appear in image 212.

Figure 3:
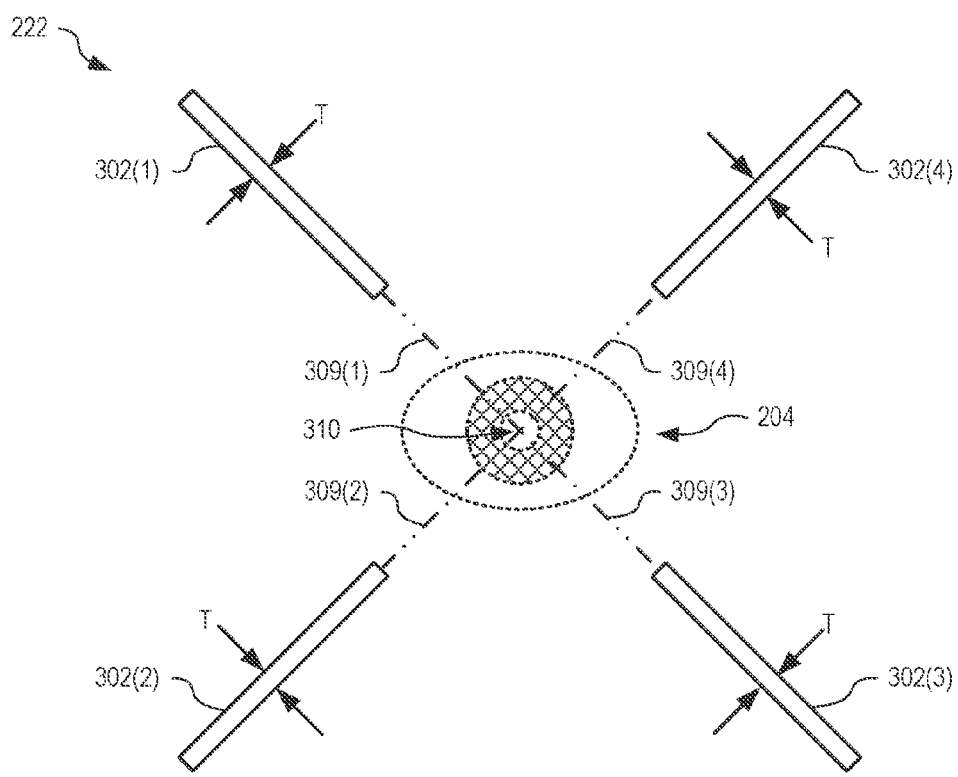
FIG. 3 shows the light pattern of FIG. 2 projected from the projector onto a flat surface.

FIG. 3 shows light pattern 222 projected from projector 220 of FIG. 2 onto a flat surface. As shown, pattern 222 has four projected lines, 302(1)-(4), none of which project onto a central area, shown with a representation of eye 204. The extensions of lines 302, illustrated by dashed lines 309(1)-(4), intersect at point 310 to indicate the position of optical axis 206 of camera 208. An operator of smartphone 202 utilizes pattern 222 to align smartphone 202 such that a pupil of eye 204 (and thereby the retina (not shown), coincides with point 310, and thereby with optical axis 206.

Figure 4:
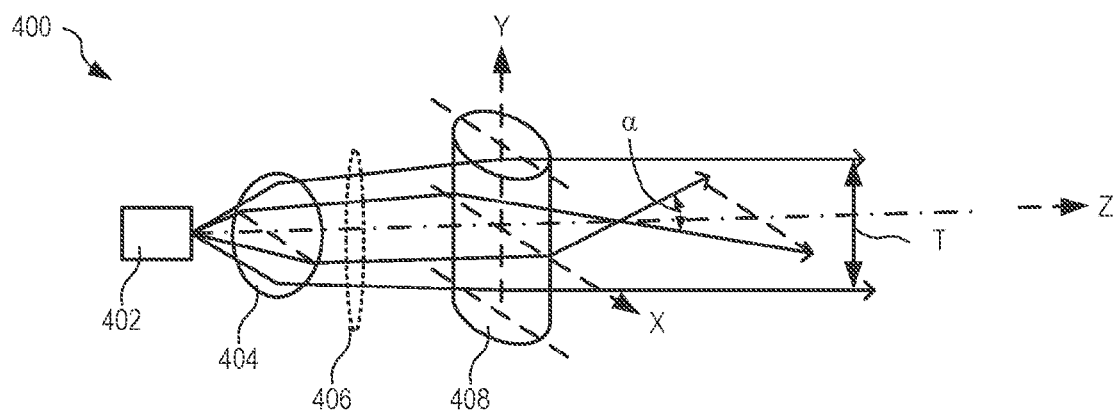
FIG. 4 is a schematic illustrating one exemplary laser line generator for use in the projector of FIG. 2, in an embodiment.

FIG. 4 is a schematic illustrating one exemplary laser line generator 400 for use in projector 220 of FIG. 2. Four laser line generators 400 are configured within projector 220 and are positioned to generate lines 302 of FIG. 3.

Figure 5:
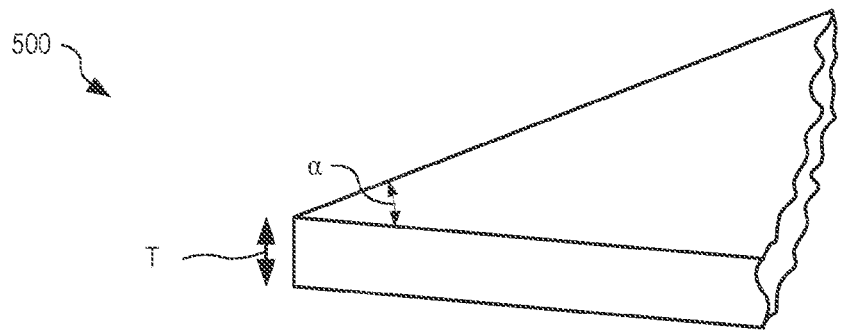
FIG. 5 shows a cylindrical sector shaped light pattern generated by the laser line generator of FIG. 4, in an embodiment.

Laser line generator 400 includes a laser 402 (e.g., a laser diode), a spherical lens 404, and a convex cylindrical lens 408. Light emitted from laser 402 is collimated by spherical lens 404 to form collimated light 406. Collimated light 406 is focused in a plane parallel to the X-Z plane by cylindrical lens 408. The focused light then expands in the X-Z plane with an angle α. After passing through cylindrical lens 408, the light from laser 402 is still collimated in an orthogonal direction Y, and has a beam width T in a Y direction. FIG. 5 shows a cylindrical sector (e.g., pizza) shaped light pattern 500 generated by laser line generator 402 parallel to the X-Z plane. When the light pattern 500 is projected onto a planar surface, a bright line appears on that surface. Beam width T of light pattern 500 is determined by the size of the collimated light after passing through spherical lens 404. The angle α of light pattern 500 is determined by cylindrical lens 408. In an alternate embodiment, a concave cylindrical lens may be used in place of convex cylindrical lens 408. However, convex cylindrical lens with a circular cross-section may be easier to manufacture and therefore less expensive.

As shown in FIG. 3, beam width T of light pattern 500 corresponds to a width of lines 302. Angle α of light pattern 500 determines a length of lines 302 when projected onto a surface, such as the face of subject 205.

Figure 6:
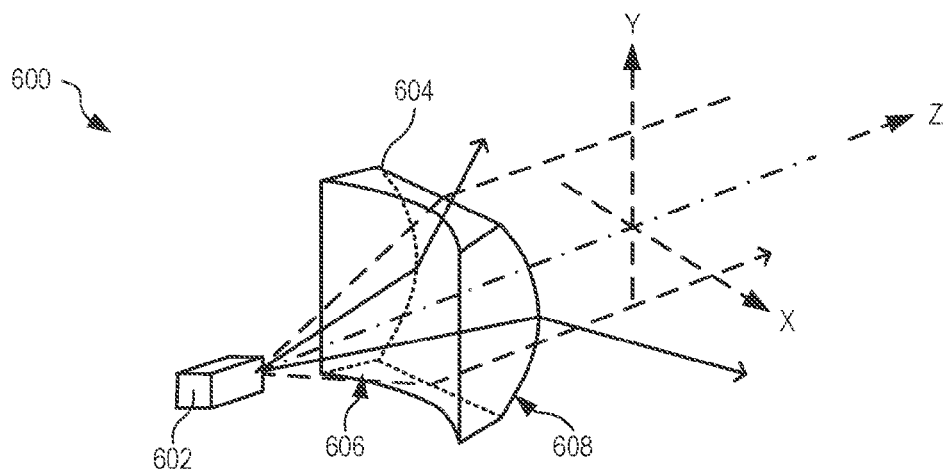
FIG. 6 shows one exemplary laser line generator that has a laser and a single lens, in an embodiment.

FIG. 6 shows one exemplary laser line generator 600 that includes a laser 602 (e.g., a laser diode) and a single lens 604. Single lens 604 has a first cylindrically curved surface 606 nearest laser 602 and a second cylindrically curved surface 608 that is orthogonal to, and opposite, cylindrically curved surface 606. First cylindrically curved surface 606 is concave and functions to spread light from laser 602 relative to plane X-Z. Second cylindrically curved surface 608 is convex and functions to collimate light in an orthogonal plane Y-Z. Laser line generator 600 thereby generates light similar to light pattern 500.

Figure 7:
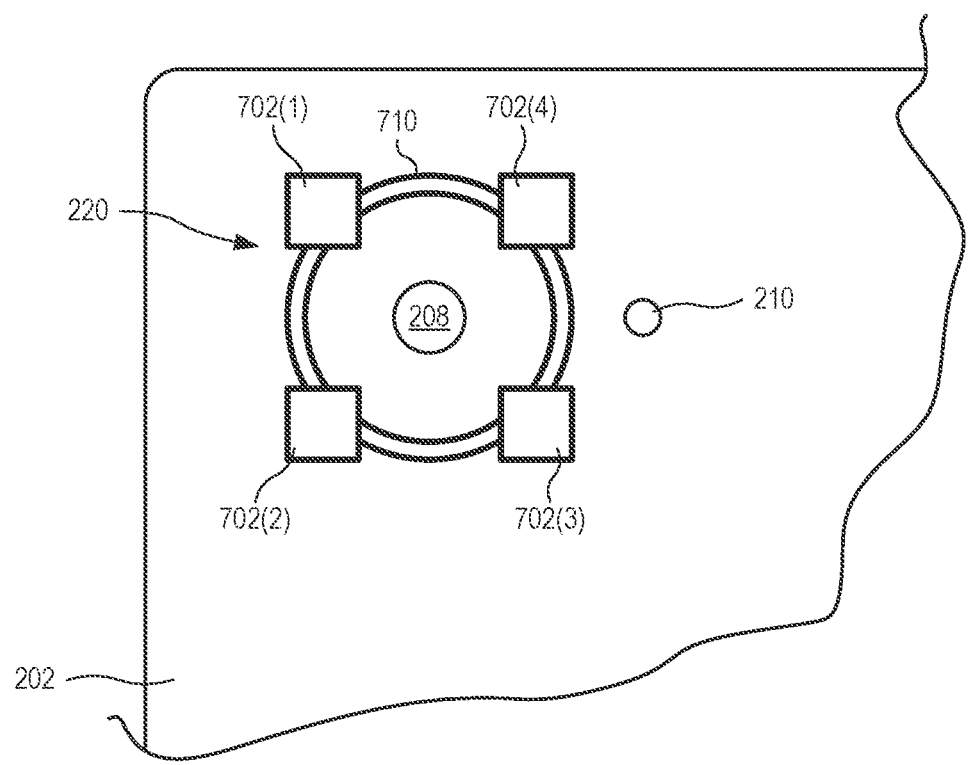
FIG. 7 shows the projector of FIG. 2 formed with four exemplary laser line generators, in an embodiment.

FIG. 7 shows projector 220 of FIG. 2 formed with four exemplary laser line generators 702(1)-(4) disposed around camera 208 of smart phone 202 and supported by a structure 710. Laser line generators 702 may be implemented as one or both of laser line generator 400 of FIG. 4 and laser line generator 600 of FIG. 6. Line generators 702 and structure 710 are configured to not block flashlight 210 of the smart-phone 202 which may be used to illuminate eye 204 during capture of image 212. Structure 710 positions laser line generators 702 such that the light pattern (e.g., light pattern 222 of FIG. 2) generated by generators 702 is optically aligned with optical axis 206 of camera 208.

Structure 710 is shown substantially circular, but may have any enclosing shape without departing from the scope hereof. Projector 220 (i.e., structure 710 and/or laser line generators 702) may be attached to smart-phone 202 using one or more of a clip, a hook, adhesive, and other fastening methods known to one of ordinary skill in the art.

Although shown with four laser line generators 702, projector 220 and structure 710 may be configured with two or more laser line generators 702 without departing from the scope hereof.

Structure 710 may be further configured to hold a macro lens (not shown) positioned in front of camera 208 for capturing image 212 of eye 204 when distance D is less than a minimum focusing distance of camera 208. Similarly, structure 710 may be further configured to hold a telephoto lens (not shown) to enable camera 208 to capture image 212 of eye 204 when distance D is long. Although shown capturing images of eye 204, smart-phone 202 and projector 220 may be used to capture images of any object where precise positioning of camera 208 is desired and is not limited to only capturing images of the eye. Smart-phone 202 and projector 220 may also be used for taking an image of iris for iris recognition and biometric identification.

Figure 8:
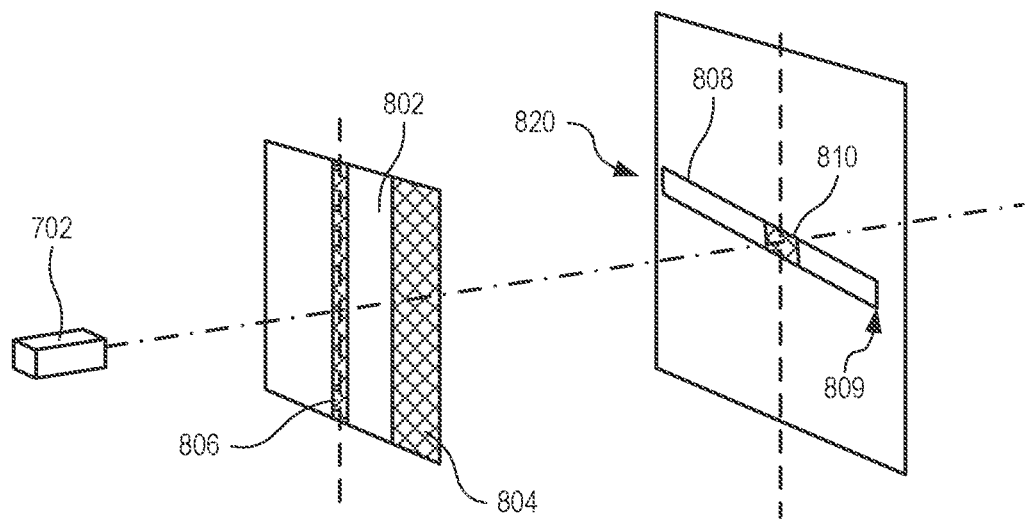
FIG. 8 shows the laser line generator of FIG. 7 further configured with a mask, in an embodiment.

FIG. 8 shows laser line generator 702 of FIG. 7 further configured with a mask 802 operable to block at least part of light from laser line generator 702. Mask 802 is substantially transparent apart from an opaque area 804 and an opaque line 806. Opaque area 804 blocks light to form end 809 of projected line 808 to prevent illumination of eye 204 by light from line generator 800. Opaque line 806 is positioned to block a portion of light from laser line generator 800 to form a dark spot 810 on projected line 808, which may allow a user to estimate the distance D of eye 204 from camera 208 of smart phone 202.

Figure 9:
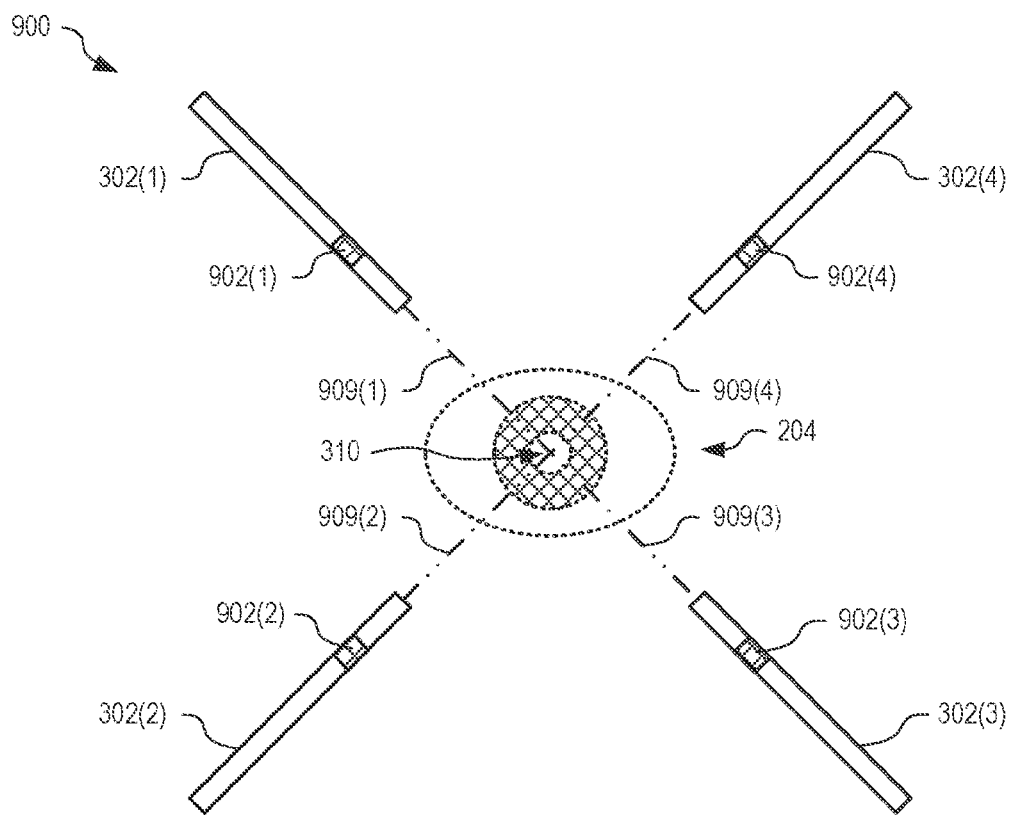
FIG. 9 shows one exemplary projected light pattern, generated by the projector of FIG. 2, which is similar to the light pattern of FIG. 3, except that each line includes a dark spot.

FIG. 9 shows one exemplary projected light pattern 900, generated by the projector of FIG. 2, which is similar to light pattern 300 of FIG. 3, except that each line 302(1)-(4) includes a dark spot 902(1)-(4), respectively. These dark spots 902 are used to estimate the distance D of the eye 204 from camera 208 of the smart phone 202. When the eye 204 is further away from camera 208 of the smart-phone 202, the dark spots 902 are also further away from the eye 204. When adjusting the distance D, the alignment of the eye is maintained by keeping eye 204 at the intersection of the extensions of lines 302. When the subject's face is substantially parallel to the smart-phone 202, the lines 302 are symmetrical around eye 204. If the lines 302 are not symmetrical, position of smart-phone 202 is adjusted until the lines 302 become symmetrical around eye 204.

Figure 10:
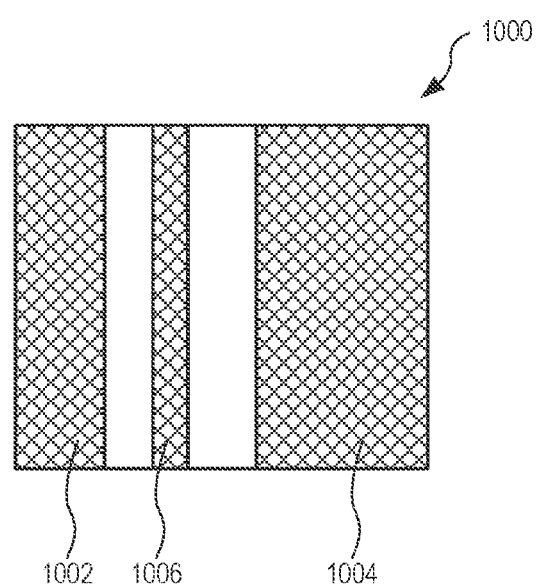
FIG. 10 shows one exemplary mask configured with a first area, a second area, and a bar, for use in the projector of FIG. 2, in an embodiment.
Figure 11:
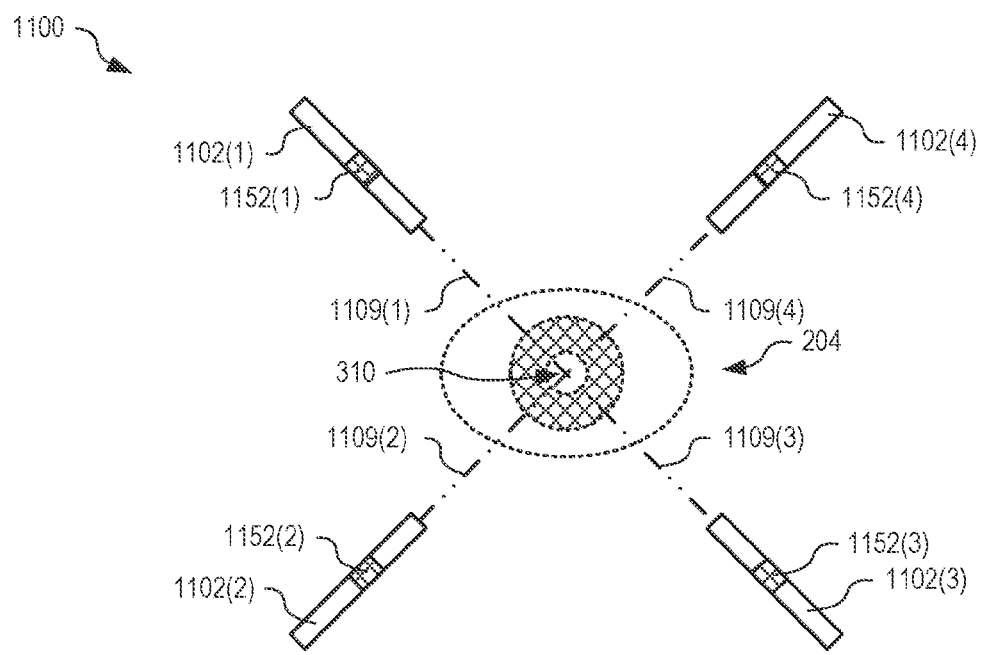
FIG. 11 shows one exemplary light pattern generated by the mask of FIG. 10, in an embodiment.

FIG. 10 shows one exemplary mask 1000 configured with a first area 1002, a second area 1004, and a bar 1006, for use in projector 220 of FIG. 2. Mask 100 may be used in place of mask 802 of FIG. 8, for example. FIG. 11 shows one exemplary light pattern 1100 generated by mask 1000 of FIG. 10. FIGS. 10 and 11 are best viewed together with the following description.

Light pattern 1100 is similar to light pattern 300 of FIG. 3, but lines 1102(1)-(4) are shortened by opaque areas 1002 and 1004 of mask 1000, and dark spots 1152(1)-(4) are formed by stripe 1106.

Figure 12:
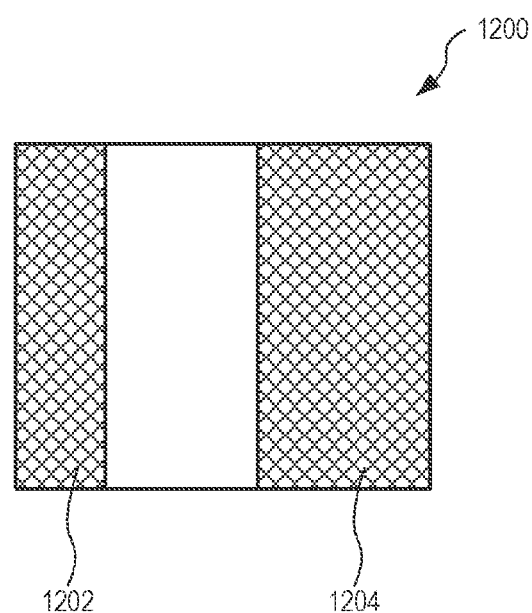
FIG. 12 shows one exemplary mask that is similar to the mask of FIG. 10 except that the opaque line is removed leaving two opaque areas that correspond to the two opaque areas of the mask of FIG. 10.

FIG. 12 shows one exemplary mask 1200 that is similar to mask 1000 of FIG. 10 except that opaque line 1006 is removed leaving the opaque areas 1202 and 1204, where areas 1202 and 1204 corresponds to areas 1002 and 1004 of mask 1000, respectively. Using mask 1200 in place of mask 1000 within projector 220 results in a pattern similar to that of FIG. 11, except that the dark spots 1152 are removed.

In one embodiment, structure 710 of FIG. 7 is implemented as a smartphone case that functions to protect smartphone 104 and to position laser line generators 702 relative to camera 208.

Using projector 220, a person (e.g., subject 205) is able take image 212 of his/her own eye by using a mirror to position pattern 222, and this smartphone 202, relative to his/her own face. The person may then send image 212 to a doctor (at a distance) for medical evaluation. Thus, the user and the subject may be one and the same.

Combination of Features

Features described above as well as those claimed below may be combined in various ways without departing from the scope hereof. The following examples illustrate some possible, non-limiting combinations:

(A1) A projector for adaptor-less smartphone eye imaging, includes at least two line generators for projecting a light pattern onto a face of a subject, and a structure for positioning the line generators relative to a camera of the smartphone. The light pattern is configured to facilitate positioning of the smartphone relative to the subject's eye such that an image of the eye captured by the camera is optimal for evaluation.

(A2) In the projector denoted by (A1), the at least two line generators being positioned proximate the camera to optically align the light pattern with the optical axis of the camera.

(A3) In the projectors denoted by one of (A1) and (A2), when the camera is positioned to capture the optimal image, the light pattern comprising at least two lines that appear on the subject's face and do not illuminate the subject's eye, wherein an intersection of lines extrapolated from the at least two lines intersect at a pupil of the eye.

(A4) In the projectors denoted by (A1) through (A3), each of the at least two line generators further including a mask having first opaque portion for shortening a first end of a corresponding line of the light pattern to prevent light from illuminating the subject's eye.

(A5) In the projectors denoted by (A1) through (A4), the mask further including an opaque bar for positioning a dark spot on the corresponding line, wherein the dark spot facilitates positioning the smartphone and camera at the optimal distance for capturing the image of the eye.

(A6) In the projectors denoted by (A1) through (A5), the mask further including a second opaque portion for shortening a second end of the corresponding line opposite the first end.

(A7) In the projectors denoted by (A1) through (A6), the structure forming a protective case for the smartphone.

(A8) In the projectors denoted by (A1) through (A7), the at least two line generators being controllable by an app running on the smartphone.

(A9) In the projectors denoted by (A1) through (A4), the light pattern having one or both of mirror symmetry and rotational symmetry.

(B1) A method facilitates adaptor-less smartphone eye imaging. A projector is coupled proximate a camera of a smartphone and includes at least two line generators. Within each of the at least two line generators, a pattern of light is generated that is projected into a field of view of the camera such that the pattern of light is easily seen on the face of a subject when the camera is positioned optimally for capturing an image of the subject's eye.

(B2) In the method denoted as (B1), a portion of light from each of the at least two line generators is masked such that the pattern of light does not illuminate the eye when capturing the image.

(B3) In the methods denoted as (B1) and (B2), a portion of light from at least one of the line generators is masked to form a dark spot within the pattern of light, wherein the dark spot facilitates the optimal positioning of the camera to capture the image.

(B4) In the methods denoted as (B1) through (B3), the pattern of light is generated in response to control from an app running on the smartphone.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A projector for adaptor-less smartphone eye imaging, comprising:
at least two line generators for projecting a light pattern onto a face of a subject; and
a structure for positioning the line generators relative to a camera of the smartphone;
wherein the light pattern is configured to facilitate positioning of the smartphone relative to the subject's eye such that an image of the eye captured by the camera is optimal for evaluation.

2. The projector of claim 1, the at least two line generators being positioned proximate the camera to optically align the light pattern with the optical axis of the camera.

3. The projector of claim 1, when the camera is positioned to capture the optimal image, the light pattern comprising at least two lines that appear on the subject's face and do not illuminate the subject's eye, wherein an intersection of lines extrapolated from the at least two lines intersect at a pupil of the eye.

4. The projector of claim 1, each of the at least two line generators further comprising a mask having first opaque portion for shortening a first end of a corresponding line of the light pattern to prevent light from illuminating the subject's eye.

5. The projector of claim 4, the mask further comprising an opaque bar for positioning a dark spot on the corresponding line, wherein the dark spot facilitates positioning the smartphone and camera at the optimal distance for capturing the image of the eye.

6. The projector of claim 4, the mask further comprising a second opaque portion for shortening a second end of the corresponding line opposite the first end.

7. The projector of claim 1, the structure forming a protective case for the smartphone.

8. The projector of claim 1, wherein the at least two line generators are controllable by an app running on the smartphone.

9. The projector of claim 1, wherein the light pattern has one or both of mirror symmetry and rotational symmetry.

10. The projector of claim 1, wherein the structure is configured to hold a macro lens positioned in front of the camera.

11. The projector of claim 1, wherein the structure is configured to hold a telephoto lens positioned in front of the camera.

12. A method for adaptor-less smartphone eye imaging, comprising:
- coupling a projector proximate a camera of a smartphone, the projector comprising at least two line generators; and
- generating, within each of the at least two line generators, a pattern of light that is projected into a field of view of the camera, wherein the pattern of light is easily seen on the face of a subject when the camera is positioned optimally for capturing an image of the subject's eye.

13. The method of claim 12, the step of generating further comprising masking a portion of light from each of the at least two line generators such that the pattern of light does not illuminate the eye when capturing the image.

14. The method of claim 12, the step of generating further comprising masking a portion of light from at least one of the line generators to form a dark spot within the pattern of light, wherein the dark spot facilitates the optimal positioning of the camera to capture the image.

15. The method of claim 12, the step of generating being responsive to control from an app running on the smartphone.

\* \* \* \* \*